US00PP22426P2

(12) United States Plant Patent
Heuger

(10) Patent No.: US PP22,426 P2
(45) Date of Patent: Dec. 27, 2011

(54) ***HELLEBORUS* PLANT NAMED 'COSEH 780'**

(50) Latin Name: ***Helleborus niger*×*Helleborus*×*sternii***
Varietal Denomination: COSEH 780

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 13/068,374

(22) Filed: May 9, 2011

(51) Int. Cl.
*A01H 5/00* (2006.01)

(52) U.S. Cl. ..... Plt./439

(58) Field of Classification Search ..... Plt./439
See application file for complete search history.

(56) References Cited

U.S. PATENT DOCUMENTS

PP21,003 P2 * 5/2010 Heuger ..... Plt./439
PP21,526 P2 * 11/2010 Heuger ..... Plt./439

* cited by examiner

*Primary Examiner* — Wendy C Haas
(74) *Attorney, Agent, or Firm* — C. A. Whealy

(57) ABSTRACT

A new and distinct cultivar of *Helleborus* plant named 'COSEH 780', characterized by its upright and uniformly mounded plant habit; uniform and freely flowering habit; dark green-colored leaves; long flowering period; single light green and white-colored flowers tinged with greyed red; and good garden performance.

2 Drawing Sheets

Botanical designation: *Helleborus niger*×*Helleborus*×*sternii*.

Cultivar denomination: 'COSEH 780'.

BACKGROUND OF THE INVENTION

The present invention relates to a new and distinct cultivar of *Helleborus* plant, botanically known as *Helleborus niger*×*Helleborus*×*sternii,* and hereinafter referred to by the name 'COSEH 780'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in November, 2003 of an unnamed proprietary seedling selection of *Helleborus niger,* not patented, as the female, or seed, parent with an unnamed proprietary seedling selection of *Helleborus*×*sternii,* not patented, as the male, or pollen, parent. The new *Helleborus* plant was discovered and selected by the Inventor as a single flowering plant from within the progeny of the stated cross-pollination grown in a controlled greenhouse environment in Glandorf, Germany in February, 2006.

Asexual reproduction of the new *Helleborus* plant by divisions in a controlled greenhouse environment in Glandorf, Germany since March, 2006, has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 780'. These characteristics in combination distinguish 'COSEH 780' as a new and distinct *Helleborus* plant:

1. Upright and uniformly mounded plant habit.
2. Uniform and freely flowering habit.
3. Dark green-colored leaves.
4. Long flowering period.
5. Single light green and white-colored flowers tinged with greyed red.
6. Good garden performance.

Compared to plants of the parent selections, plants of the new *Helleborus* are more uniformly mounded and are more uniformly and freely flowering.

Plants of the new *Helleborus* can be compared to plants of *Helleborus niger*×*Helleborus lividus* 'COSEH 700', disclosed in U.S. Plant Pat. No. 21,003. In side-by-side comparisons conducted in Glandorf, Germany, plants of the new *Helleborus* differed primarily from plants of 'COSEH 700' in the following characteristics:

1. Plants of the new *Helleborus* had larger flowers than plants of 'COSEH 700'.
2. Plants of the new *Helleborus* and 'COSEH 700' differed in flower color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 780' grown in a container.

The photograph on the second sheet is a close-up view of a typical flowering plant of 'COSEH 780'.

DETAILED BOTANICAL DESCRIPTION

The aforementioned photographs and following observations, measurements and values describe plants grown in 15-cm containers during the winter in a glass-covered greenhouse in Glandorf, Germany and under conditions which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus*×*sternii* 'COSEH 780'.

Parentage:

*Female, or seed, parent.*—Unnamed proprietary seedling selection of *Helleborus niger,* not patented.

*Male, or pollen, parent.*—Unnamed proprietary seedling selection of *Helleborus*×*sternii,* not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and uniformly mounding plant habit with flowers held just above the foliar plane; plant shape is globular; and moderately vigorous growth habit.

*Plant height.*—About 33.4 cm.

*Plant diameter* (*area of spread*).—About 43.1 cm.

Foliage description:

*Arrangement.*—Leaves arranged in a basal rosette; leaves palmately compound with five leaflets per leaf.

*Leaf length.*—About 16.5 cm.

*Leaf width.*—About 18.9 cm.

*Leaflet length.*—About 11.8 cm.

*Leaflet width.*—About 5.2 cm.

*Leaf shape.*—Palmate; orbicular in outline.

*Leaflet shape.*—Ovate to elliptic.

*Leaflet apex.*—Acute.

*Leaflet base.*—Attenuate.

*Leaflet margin.*—Sharply serrate.

*Leaflet texture, upper and lower surfaces.*—Smooth, glabrous; leathery.

*Leaflet venation pattern.*—Pinnate.

*Leaflet color.*—Developing leaves, upper surface: Close to N137B. Developing leaves, lower surface: Close to 147B. Fully developed leaves, upper surface: Close to 147A; venation, close to 151 A to 151 B. Fully developed leaves, lower surface: Close to 148A; venation, close to 176A to 176B.

*Petiole.*—Length: About 7.7 cm. Diameter: About 6 mm. Texture, upper and lower surfaces: Smooth, glabrous. Color, upper and lower surfaces: Close to 146C to 146D; moderately to heavily tinged and dotted with close to 200C to 200D.

Flower description:

*Flower shape and habit.*—Single rotate flowers arranged in terminal and axillary cymes; freely and uniform flowering habit with about 60 flowers and flower buds per plant; flowers facing outwardly to slightly nodding and slightly upright.

*Fragrance.*—None detected.

*Natural flowering season.*—Plants begin flowering about ten months after planting; long flowering period; plants flower from late winter to early spring in Germany.

*Flower longevity on the plant.*—About ten days; flowers not persistent.

*Flower buds.*—Length: About 1.9 cm. Diameter: About 1.3 cm. Shape: Obovate. Color: Between 145C to 145D and 149D; towards the base, tinged with close to 177C to 177D.

*Inflorescence height.*—About 27.1 cm.

*Inflorescence diameter.*—About 41.4 cm.

*Flower diameter.*—About 6.1 cm.

*Flower depth* (*height*).—About 2.2 cm.

*Petals.*—Transformed into nectaries.

*Sepals.*—Quantity and arrangement: Five arranged in a single whorl. Length: About 3.5 cm. Width: About 2.6 cm. Shape: Ovate to broadly obovate. Apex: Rounded. Margin: Entire. Texture, upper and lower surfaces: Smooth, glabrous. Color: When opening, upper surface: Close to 145C; towards the base, close to 144C. When opening, lower surface: Close to 145C to 145D; center strongly tinged with close to between 177C to 177D and 182B to 182C. Fully opened, upper surface: Close to 145C slightly tinged with close to 182D; towards the margins, close to 145D and 157A to 157B; towards the base, close to 144C; with development, color becoming closer to 144A. Fully opened, lower surface: Close to 145C to 145D; center moderately to strongly tinged with close to between 177C to 177D and 182B to 182C.

*Peduncles.*—Strength: Moderately strong. Length: About 18.2 cm. Diameter: About 6 mm. Aspect: About 10° from vertical. Texture: Smooth, glabrous. Color: Close to 145C slightly to moderately dotted with close to 182B.

*Pedicels.*—Strength: Moderately strong. Length: About 2 cm. Diameter: About 2 mm. Aspect: Erect to about 25° from the peduncle axis. Texture: Smooth, glabrous. Color: Close to 145B to 145C tinged with close to 184B to 184C.

*Reproductive organs.*—Stamens: Quantity per flower: About 70. Filament length: About 1.5 cm. Filament color: Close to 157D. Anther shape: Reniform. Anther length: About 1.5 mm. Anther color: Close to 150B. Pollen amount: Scarce. Pollen color: Close to 158D. Pistils: Quantity per flower: About six. Pistil length: About 1.1 cm. Stigma shape: Club-shaped. Stigma color: Close to 150D. Style length: About 1 cm. Style color: Close to 150D. Ovary color: Close to 150D. Nectaries (transformed petals): Quantity per flower: About 13. Length: About 8 mm. Diameter, apex: About 2 mm. Diameter, base: About 1 mm. Shape: Flattened triangular. Color: Close to 145B; towards the base, close to 144C.

*Seeds/fruits.*—Seed and fruit development have not been observed.

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen/pest resistance: Plants of the new *Helleborus* have not been shown to be resistant to pathogens and pests common to *Helleborus*.

It is claimed:

1. A new and distinct *Helleborus* plant named 'COSEH 780' as illustrated and described.

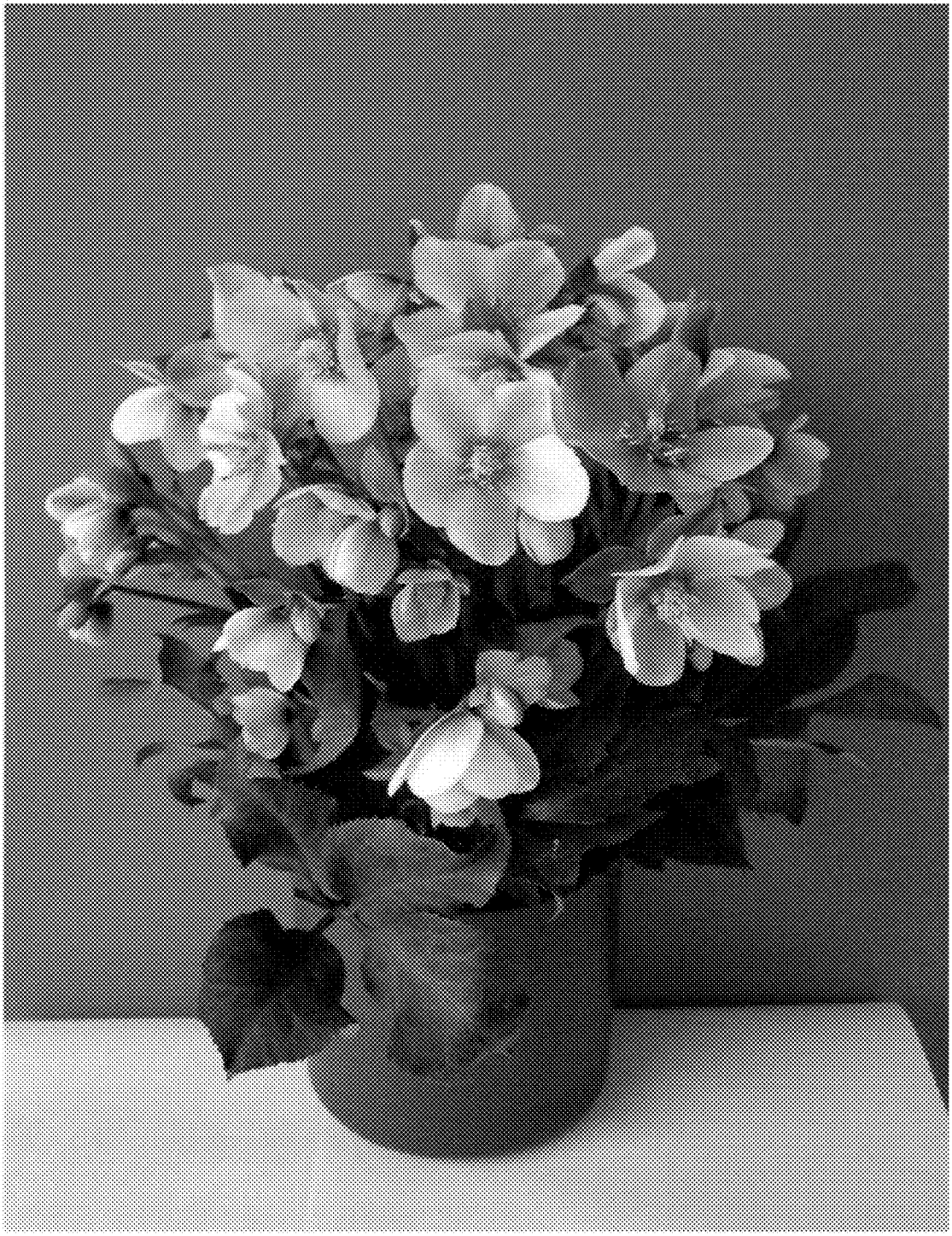

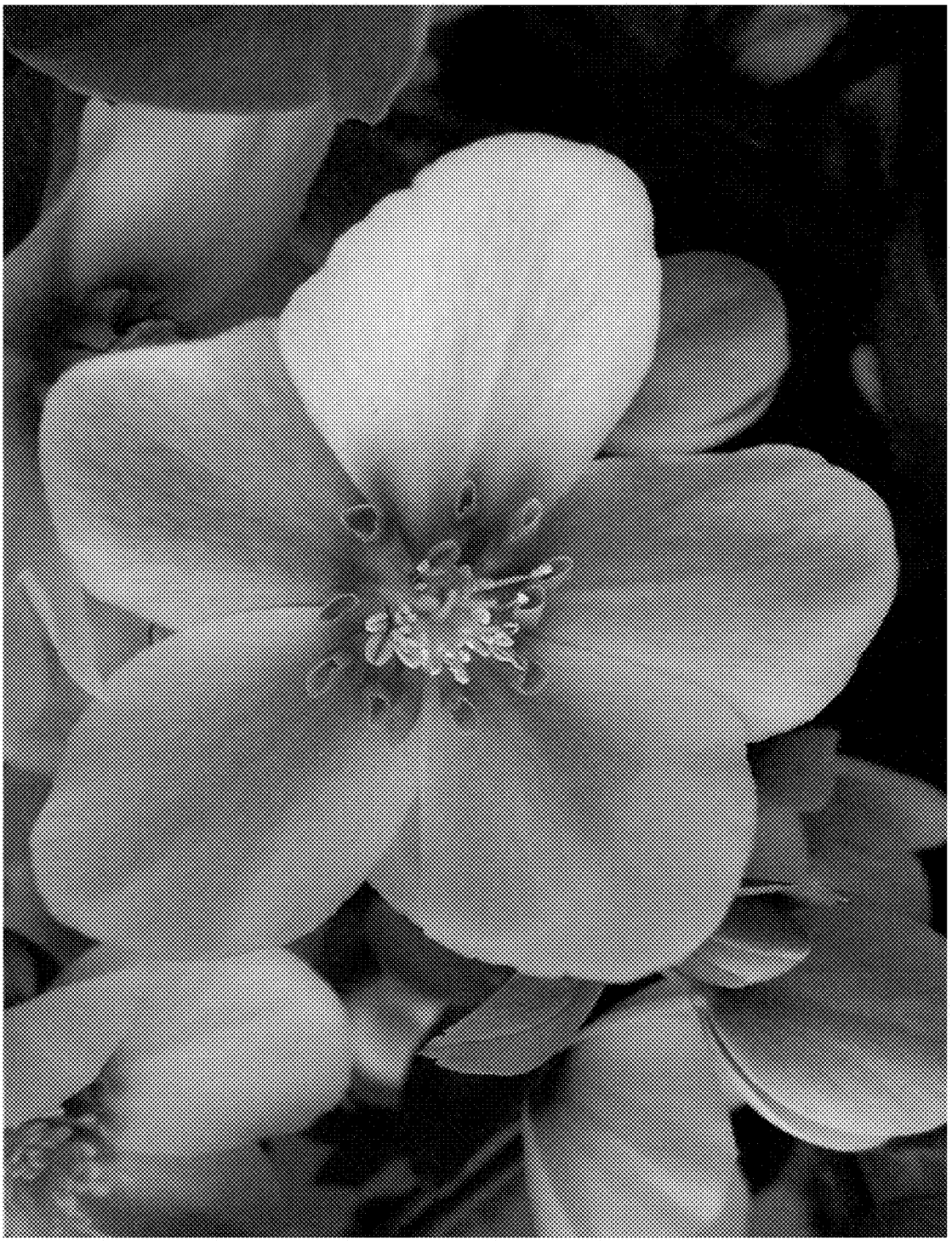

* * * * *